(12) United States Patent
Crisci et al.

(10) Patent No.: US 6,353,044 B1
(45) Date of Patent: *Mar. 5, 2002

(54) LIGHT-STABILIZED ORGANIC POLYMERS

(75) Inventors: Luciana Crisci, Graffignana; Fabio Broussard, Brusaporto; Carlo Neri, S. Donato M. se; Mauro Adovasio, Bergamo, all of (IT)

(73) Assignee: Great Lakes Chemical Italia S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/423,283

(22) PCT Filed: May 7, 1998

(86) PCT No.: PCT/EP98/02678

§ 371 Date: Nov. 8, 1999

§ 102(e) Date: Nov. 8, 1999

(87) PCT Pub. No.: WO98/50360

PCT Pub. Date: Nov. 12, 1998

(30) Foreign Application Priority Data

May 8, 1997 (IT) .......................................... MI97A1064

(51) Int. Cl.[7] .................... C08K 5/3435; C08K 5/3492; C08K 5/35

(52) U.S. Cl. .......................... 524/99; 524/100; 524/102; 524/103

(58) Field of Search .......................... 524/99, 100, 102, 524/103

(56) References Cited

U.S. PATENT DOCUMENTS 4,855,434 A * 8/1989 Cantatore et al.
5,486,613 A  1/1996 Broussard et al.

FOREIGN PATENT DOCUMENTS

| DE | 2849444 | * | 5/1980 |
| DE | 3533451 | * | 3/1987 |
| EP | 0345221 | * | 12/1989 |

* cited by examiner

Primary Examiner—Tae H. Yoon
(74) Attorney, Agent, or Firm—Oblon, Spivak, McClelland, Maier & Neustadt, P.C.

(57) ABSTRACT

Compounds belonging to the group of enamines consisting of derivatives of β-keto-esters or β-keto-amides or 1,3-diketones with primary or secondary aliphatic or aromatic amines carrying at least one sterically hindered amine group having general formula (I) in the molecule. The compounds having general formula (I) can be used as antioxidants or light stabilizers for organic polymers.

9 Claims, No Drawings

LIGHT-STABILIZED ORGANIC POLYMERS

The present invention relates to light-stabilized organic polymers.

More specifically, the present invention relates to organic polymers light-stabilized by the addition, to said organic polymers, of an effective quantity of one or more compounds belonging to the group of enamines consisting of derivatives of β-keto-esters, or β-keto-amides or 1,3-diketones with primary or secondary aliphatic or aromatic amines, carrying at least one sterically hindered amine group in the molecule.

It is known that organic polymers undergo degradation over a period of time as a result of exposure to atmospheric agents, and mainly to ultraviolet radiation, and they also easily undergo thermoxidative degradation during processing and transformation processes.

This degradation causes a deterioration in the physical characteristics of organic polymers such as, for example, a reduction in the impact strenght and flexure as well as alterations in the optical properties of the end-article.

Stabilizing compounds are usually introduced into organic polymers to prevent the above degradation.

The Applicant has now found that compounds belonging to the group of enamines consisting of derivatives of β-keto-esters, or β-keto-amides or 1,3-diketones with primary or secondary aliphatic or aromatic amines, carrying at least one sterically hindered amine group in the molecule, are capable of stabilizing organic polymers to which they are added improving their resistance to light, in particular, to ultraviolet radiation.

The above compounds are capable of absorbing ultraviolet radiation with a maximum absorption at a wave-length equal to 280 nm. This wave-length has a particularly aggressive action towards organic polymers.

The present invention therefore relates to organic polymers light-stabilized by the addition, to said organic polymers, of an effective quantity of one or more compounds belonging to the group of enamines consisting of derivatives of β-keto-esters, or β-keto-amides or 1,3-diketones with primary or secondary aliphatic or aromatic amines, carrying in the molecule at least one sterically hindered amine group, having general formula (I):

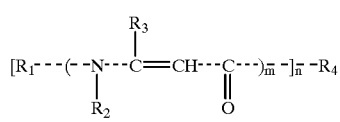

(I)

wherein m represents an integer from 1 to 3, extremes included;

n represents an integer from 1 to 4, extremes included;

$R_1$ represents a triazine having one or the following general formula (II), (III) or (IV):

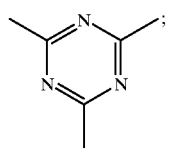

(II)

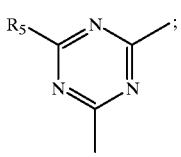

(III)

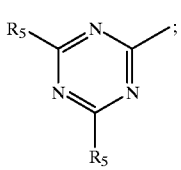

(IV)

wherein $R_5$ represents a hydrogen atom; a linear or branched $C_1$–$C_{18}$ alkyl group; a —$NHR_6$ amine group or a —$SR_6$ group wherein $R_6$ represents a hydrogen atom or a linear or branched $C_1$–$C_{18}$ alkyl group;

$R_1$ and $R_2$, the same or different, represent a hydrogen atom; a linear or branched $C_1$–$C_8$ alkyl group; a linear or branched $C_2$–$C_8$ alkoxyalkyl group; a $C_5$–$C_8$ cycloalkyl group optionally containing a heteroatom selected from oxygen, nitrogen and sulfur; a $C_6$–$C_{18}$ aryl group; a $C_7$–$C_{20}$ arylalkyl or alkylaryl group; a group having general formula (V):

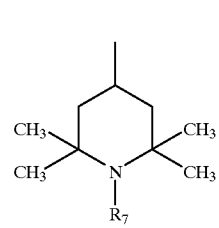

(V)

wherein $R_7$ represents a hydrogen atom; a linear or branched $C_1$–$C_{18}$ alkyl group, said alkyl group optionally substituted with a —$NHR_8$ group or an —$OR_8$ group wherein $R_8$ represents a hydrogen atom, a linear or branched $C_1$–$C_{18}$ alkyl group, or a $C_6$–$C_{18}$ aryl group; an —$OR_9$ group wherein $R_9$ represents a hydrogen atom, or a linear or branched $C_1$–$C_{18}$ alkyl group;

or, $R_1$ and $R_2$ considered jointly with the nitrogen atom, represent a $C_5$–$C_8$ heterocyclic group optionally containing a second heteroatom selected from oxygen, nitrogen and sulfur;

$R_3$ and $R_4$, the same or different, represent a linear or branched $C_1$–$C_{18}$ alkyl group; a $C_6$–$C_{18}$ aryl group; a $C_7$–$C_{20}$ alkylaryl or arylalkyl group; a linear or branched $C_1$–$C_8$ alkoxyl group;

or, $R_4$ represents a group having general formula (VI):

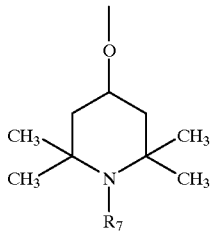
(VI)

wherein $R_7$ has the same meanings defined above;

or, $R_4$ represents an $NR_{10}R_{11}$ group wherein $R_{10}$ and $R_{11}$, the same or different, represent a hydrogen atom; a linear or branched $C_1$–$C_{18}$ alkyl group; a linear or branched $C_2$–$C_8$ alkoxyalkyl group; a $C_5$–$C_8$ cycloalkyl group optionally containing a heteroatom selected from oxygen, nitrogen and sulfur; a $C_6$–$C_{15}$ aryl group; a $C_7$–$C_{20}$ arylalkyl or alkylaryl group; a triazine having one of the following general formula (II), (III) or (IV):

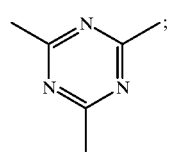
(II)

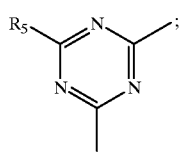
(III)

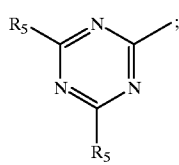
(IV)

wherein $R_5$ has the same meanings defined above; a group having general formula (V);

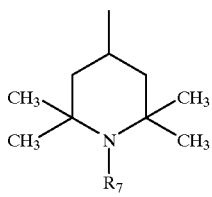
(V)

wherein $R_7$ has the same meanings defined above;

or, $R_{10}$ and $R_{11}$ considered jointly with the nitrogen atom, represent a $C_5$–$C_8$ heterocyclic group optionally containing a second heteroatom selected from oxygen, nitrogen and sulfur;

or $R_4$ represents a group having one of the following general formulae (VII), (VIII) or (IX):

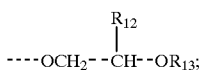
(VII)

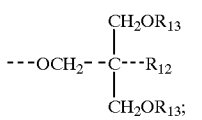
(VIII)

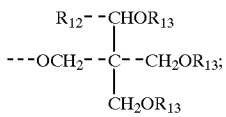
(IX)

wherein:
$R_{12}$ represents a hydrogen atom; or a linear or branched $C_1$–$C_{18}$ alkyl group;
$R_{13}$ represents a linear or branched $C_1$–$C_8$ alkyl group; a —$COCH_2COCH_3$ group; or a direct bond;
provided that, when $R_1$ and $R_2$ are different from the group having general formula (V), $R_4$ represents a group having general formula (VI).

Examples of $R_1$, $R_2$, $R_{10}$ and $R_{11}$ groups, as well as a hydrogen atom are: methyl, ethyl, propyl, isopropyl, butyl, octyl, cyclohexyl, benzyl, phenyl, ethylphenyl, methoxyethyl, 4-(2,2,6,6-tetramethyl)piperidinyl, 4-(2,2,6,6-tetramethyl)-1-butoxyethylpiperidinyl, 4-(2,2,6,6-tetramethyl)-1-butoxypiperidinyl, 4-(2,2,6,6-tetramethyl)-1-methylpiperidinyl, 3,5-dioctylaminotriazine, 3,5-dibutylaminotriazine, etc.

Examples of $C_5$–$C_8$ heterocyclic groups, when $R_1$ and $R_2$ or $R_{10}$ and $R_{11}$ are considered jointly with the nitrogen atom, are: morpholine, pyrrolidine, piperidine, piperazine, thiomorpholine, thiazolidine, benzothiazolidine, etc.

Examples of $R_3$ and $R_4$ groups are: methyl, ethyl, propyl, isopropyl, phenyl, oxymethyl, oxyethyl, oxybutyl, etc.

Examples of $R_4$ groups, when $R_4$ represents a group having general formula (VI), are: 4-(2,2,6,6-tetramethyl)piperidinoxy, N-methyl-4-(2,2,6,6-tetramethyl)piperidinoxy, N-methoxyethyl-4-(2,2,6,6-tetramethyl)piperidinoxy, N-methylaminoethyl-4-(2,2,6,6-tetramethyl)piperidinoxy, etc.

Examples of $R_4$ groups, when $R_4$ represents a group having general formula (VII), (VIII) or (IX) and n is 2, are:

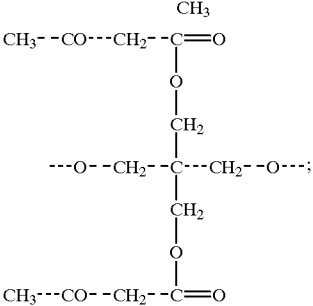

etc.

Examples of $R_4$ groups, when $R_4$ represents a group having general formula (VII), (VIII) or (IX) and n is 3, are:

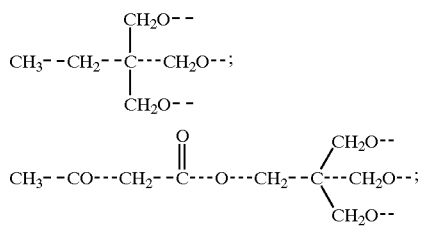

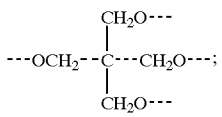

etc.

Examples of $R_7$ groups are: methyl, ethyl, propyl, butyl, ethoxy, butoxy, β-hydroxyethyl, β-methoxyethyl, β-butoxyethyl, methylaminoethyl, etc.

Examples of $R_5$, $R_6$, $R_8$, $R_9$, $R_{12}$ and $R_{13}$ groups, when said groups represent a linear or branched $C_1$–$C_{18}$ alkyl group, are: methyl, ethyl, propyl, isopropyl, butyl, octyl, etc.

Specific examples of compounds having general formula (I) which can be used for the purposes of the present invention but which should in no way be considered as limiting the its scope, are:

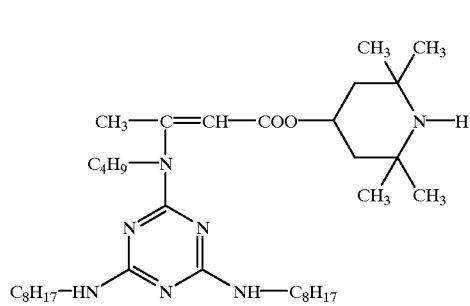

etc.

Examples of $R_4$ groups, when $R_4$ represents a group having general formula (VII), (VIII) or (IX) and n is 4, are:

(IA)

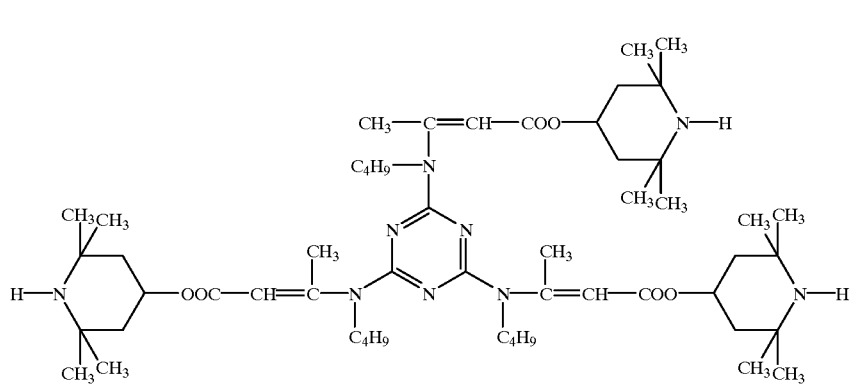

(IB)

(IC)

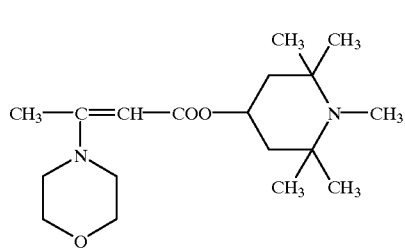

(ID)

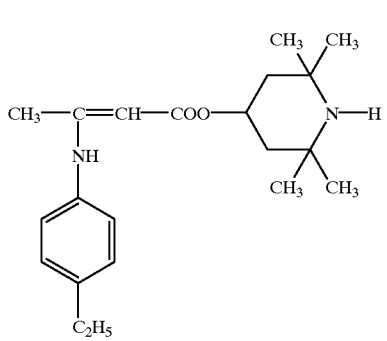

-continued

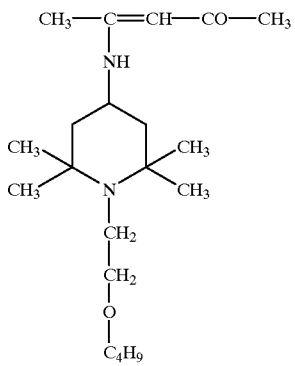
(IE)

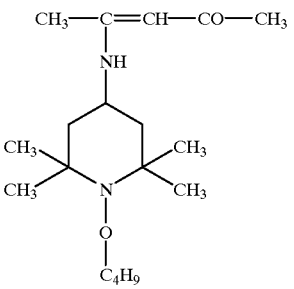
(IF)

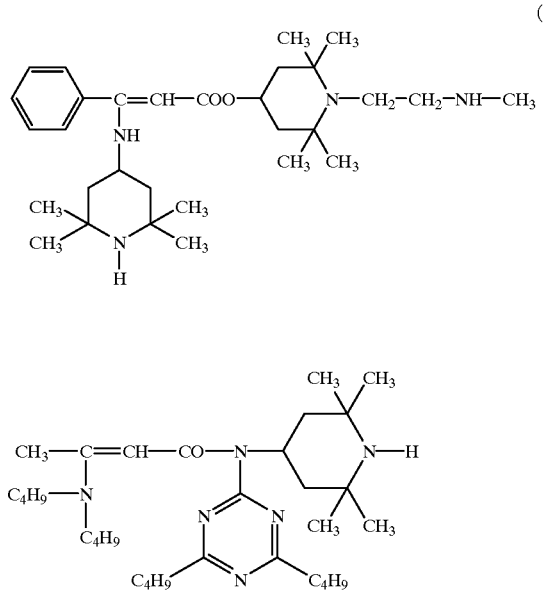
(IG)

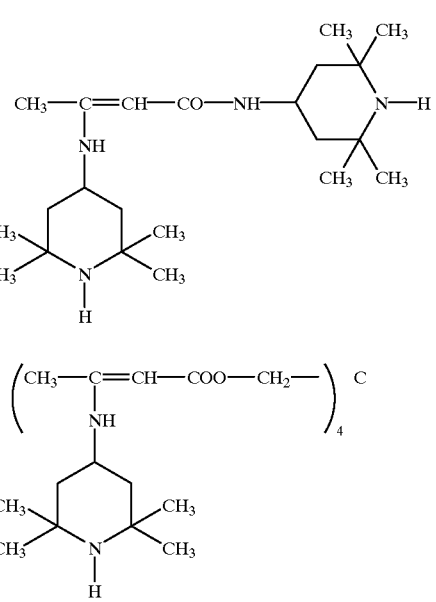
(IH)

(II)

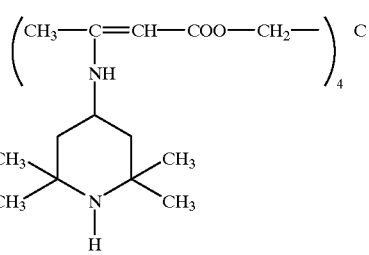
(IL)

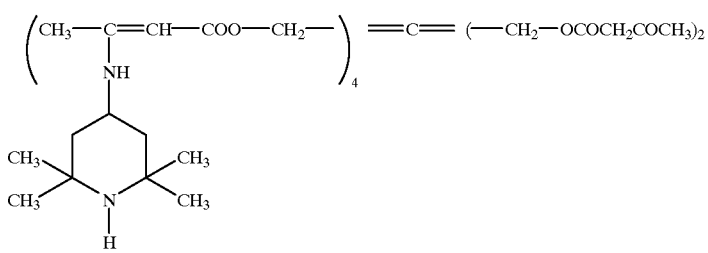
(IM)

The compounds having general formula (I) described above can be obtained with various processes.

A process for the synthesis of the compounds having general formula (I) of the present invention comprises the reaction of 1–4 moles of a primary or secondary, aliphatic or aromatic amine, having general formula (X):

$$HNR_1R_2 \qquad (X)$$

wherein $R_1$ and $R_2$ have the same meanings defined above, with 1–3 moles of a β-keto-ester, or a β-keto-amide, or a 1,3-diketone having general formula (XI):

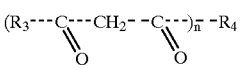
(XI)

wherein $R_3$, $R_4$ and n have the same meanings defined above.

The above reaction takes place in the presence of an inert organic solvent, preferably a hydrocarbon, in particular toluene, at a temperature ranging from 60° C. to 160° C., preferably from 115° C. to 150° C., at atmospheric pressure, and for a time ranging from 0.5 to 24 hours, preferably from 3 to 10 hours. Acetic acid can optionally be added as catalyst to this reaction.

During the above reaction, reaction water is released and is separated by azeotropic distillation using an apparatus for the azeotropic distillation, whereas the organic solvent is recycled.

At the end of the reaction, the solvent and possible acetic acid present are removed by distillation thus obtaining a raw product. The desired compound having general formula (I) is purified from the raw product thus obtained by fractionated distillation, operating under vacuum, at a pressure ranging from 0.1 mm/Hg to 50 mm/Hg and a temperature ranging from 40° C. to 200° C. Or said compound having general formula (I) is separated by crystallization using techniques known in the art.

Examples of primary or secondary, aliphatic or aromatic amines, having general formula (X) which can be used for the purposes of the present invention are: cyclohexylamine, n-butylamine, tert-butylamine, n-octylamine, tert-octylamine, n-octadecylamine, n-dodecylamine, benzylamine, 2-methoxyethylamine, 2-furfurylamine, pyrrolidine, piperidine, morpholine, dibenzylamine, aniline, diphenylamine, melamine, 4-amino-2,2,6,6-tetramethylpiperidine, 4-amino-2,2,6,6-tetramethyl-1-methylpiperidine, 4-amino-2,2,6,6-tetramethyl-1-butoxyethylpiperidine, 1-amino-3,5-dioctylaminotriazine, etc.

Examples of β-keto-esters or β-keto-amides, or 1,3-diketones having general formula (XI) which can be used for the purposes of the present invention are: ethyl acetoacetate, t-butyl acetoacetate, octadecyl acetoacetate, ethyl benzoylacetate, acetylacetone, benzoylacetone, methane dibenzoyl, p-toluylacetone, 4-(2,2,6,6-tetramethyl) piperidinyl acetoacetate, N-methyl-4-(2,2,6,6-tetramethyl) piperidinyl acetoacetate, acetoacetamide, acetoacetanilide, acetoacet-4-(2,2,6,6,-tetramethylpiperidine)amide, acetoacet-(3,5-dibutyltriazine)-1-amide, etc.

The enamine function of the compounds having general formula (I) synthesized by means of the process described above, is confirmed by NMR spectrometry analysis (obtained using a BRUKER AC 200 spectrometer) executed on samples with a high purity (95% confirmed by gas-chromatography).

Other processes which can be used for the preparation of the compounds having general formula (I) of the present invention, however, are described in literature such as, for example, in Houben-Weyl (1957), Vol. 11/1, pages 172–178.

Organic polymers capable of being light-stabilized with the compounds having general formula (I) described above, are:

(1) polymers of mono-olefins and diolefins such as, for example, polypropylene, polyisobutylene, polybut-1-ene, poly-4-methylpent-1-ene, polyisoprene or polybutadiene; as well as polymers of cyclo-olefins such as, for example, cyclopentene or norbornene; polyethylene (which can be optionally cross-linked) such as, for example, high density polyethylene (HDPE), low density polyethylene (LDPE), linear low density polyethylene (LLDPE), branched low density polyethylene (BLDPE).

The polyolefins such as, for example the mono-olefins cited in the previous paragraph, preferably polyethylene and polypropylene, can be prepared with various methods known in literature, preferably using the following methods:

(a) radicalic polymerization (generally carried out at a high pressure and high temperature;
(b) catalytic polymerization using a catalyst which normally contains one or more metals of groups IVb, Vb, VIb or VIII of the Periodic Table. These metals generally have one or more ligands such as, for example, oxides, halides, alcoholates, ethers, amines, alkyls, alkenyls and/or aryls which can be π- or σ-co-ordinated. These metal complexes can be in free form or supported in substrates such as, for example activated magnesium chloride, titanium (III) chloride, alumina or silicon oxide. These catalysts can be soluble or insoluble in the reaction medium. The catalysts can be used alone or in the presence of other activators such as, for example, metal alkyls, metal hydrides, halides of metal alkyls, oxides of metal alkyls or metal alkyloxanes, these metals being elements belonging to groups Ia, IIa and/or IIIa of the Periodic Table. The activators can be conveniently modified with other ester, ether, amine or silyl-ether groups. These catalytic systems are usually called Phillips, Standard Oil Indiana, Ziegler (-Natta), TNZ (DuPont), metallocene or "single site catalyst" (SSC).

(2) Mixtures of the polymers described under point (1) such as, for example, mixtures of polypropylene with polyisobutylene; mixtures of polypropylene with polyethylene (for example, PP/HDPE, PP/LDPE); mixtures of different types of polyethylene (for example, LDPE/HDPE).

(3) Copolymers of mono-olefins and diolefins with each other or with other vinyl monomers such as, for example, ethylene-propylene copolymers, linear low density polyethylene (LLDPE) and its mixtures with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with polypropylene and a diene such as, for example, hexadiene, dicyclopentadiene or ethylidene-norbornene; and mixtures of these copolymers with each other or with the polymers cited in paragraph (1) such as, for example, polypropylene/ethylenepropylene copolymers, LDPE/ethylene-vinylacetate (EVA) copolymers, LDPE/ethylene-acrylic acid (EAA) copolymers, LLDPE/EVA, LLDPE/EAA, and alternating or "random" polyalkylene/carbon monoxide copolymers and their mixtures with other polymers such as, for example, polyamides.

(4) Hydrocarbon resins (for example, $C_5$–$C_9$) comprising their hydrogenated modifications (for example, adhesive agents) and mixtures with polyalkylene and starch.

(5) Polystyrene, poly(p-methylstyrene), poly(α-methylstyrene).

(6) Copolymers of styrene or α-methylstyrene with dienes or acrylic derivatives such as, for example, styrene/butadiene, styrene/acrylonitrile, styrene/alkyl methacrylate, styrene/butadiene/ alkyl acrylate, styrene/butadiene/alkyl methacrylate, styrene/maleic anhydride, styrene/acrylonitrile/methylacrylate; mixtures, having a high impact strength, between copolymers of styrene and another polymer such as, for example, a polyacrylate, a polymer of a diene or an ethylene/propylene/diene terpolymer, block polymers of styrene such as, for example, styrene/butadiene/styrene, styrene/isoprene/styrene, styrene/ethylene/butylene/styrene or styrene/ethylene/propylene/styrene.

(7) Grafted copolymers of styrene or α-methylstyrene such as, for example, styrene in polybutadiene, styrene in polybutadiene or polybutadiene-acrylonitrile copolymers; styrene and acrylonitrile (or methacrylonitrile) in polybutadiene;

styrene, acrylonitrile and methylmethacrylate in polybutadiene; styrene and maleic anhydride in polybutadiene; styrene, acrylonitrile and maleic anhydride or maleimide in polybutadiene; styrene and maleimide in polybutadiene; styrene and alkylacrylates or methacrylates in polybutadiene; styrene and acrylonitrile in ethylene/propylene/diene terpolymers, styrene and acrylonitrile in polyalkyl acrylates or polyalkyl methacrylates, styrene and acrylonitrile in acrylate/butadiene copolymers, as well as mixtures of the copolymers listed above with the copolymers cited under point (6) such as, for example, mixtures of known copolymers such as ABS, MBS, ASA or AES;

(8) Polymers containing halogens such as, for example, polychloroprene, chlorinated rubbers, chlorinated or sulfochlorinated polyethylene, ethylene and chlorinated ethylene copolymers, homopolymers and copolymers of epichlorohydrin, in particular polymers of vinyl compounds containing halogens such as, for example, polyvinyl chloride, polyvinylidenechloride, polyvinyl fluoride or polyvinylidenefluoride; and also their copolymers such as, for example, vinyl chloride/vinylidenechloride, vinyl chloride/vinyl acetate or vinylidenechloride/vinyl acetate.

(9) Polymers deriving from $\alpha,\beta$-unsaturated acids and their derivatives such as, for example, polyacrylates and polymethacrylates, polymethyl methacrylates, polyacrylamides and polyacrylonitriles, modified with butyl acrylate.

(10) Copolymers of monomers according to point (9) with each other or with other unsaturated monomers such as, for example, acrylonitrile/butadiene copolymers, acrylonitrile/alkylacrylate copolymers, acrylonitrile/alkoxyalkyl acrylate copolymers or acrylonitrile/vinyl halide copolymers or acrylonitrile/alkyl methacrylate/butadiene terpolymers.

(11) Polymers deriving from unsaturated alcohols and amines, or their acyl or acetal derivatives such as, for example, polyvinyl alcohol, polyvinyl acetate, polyvinyl stearate, polyvinyl benzoate, polyvinyl maleate, polyvinyl butyrral, polyallyl phthalate or polyallyl melamine; and also their copolymers with the olefins listed under point (1).

(12) Homopolymers and copolymers of cyclic ethers such as, for example, polyalkylene glycols, polyethylene oxide, polypropylene oxides, or copolymers of the compounds described above with bis-glycidyl ethers.

(13) Polyacetals such as, for example, polyoxymethylene and polyoxymethylenes which contain ethylene oxide as comonomer; polyacetals modified with thermoplastic polyurethanes, acrylates or MBS.

(14) Polyphenylene oxides and sulfides and mixtures of polyphenylene oxides with styrene or polyamide polymers.

(15) Polyurethanes deriving from hydroxyl-terminated polyethers, polyesters or polybutadienes on the one hand and aliphatic or aromatic polyisocyanates on the other, as well as the precursors of the above compounds.

(16) Polyamides and copolyamides deriving from diamines and dicarboxylic acids and/or aminocarboxylic acids or from the corresponding lactams such as, for example, polyamide 4, polyamide 6, polyamide 6/6, 6/10, 6/9, 6/12, 4/6, 12/12, polyamide 11, polyamide 12, aromatic polyamides obtained starting from m-xylene diamine and adipic acid; polyamides prepared from hexamethylenediamine and isophthalic and/or terephthalic acid and with or without an elastomer as modifier, for example, poly-2,4,4-trimethylhexamethylene terephthalamide or poly-m-phenylene isophthalamide; and also block copolymers of the above polyamides with polyolefins, olefinic copolymers, ionomers or elastomers chemically bound or grafted; or with polyethers such as, for example, polyethylene glycol, polypropylene glycol or polytetramethylene glycol; as well as polyamides or copolyamides modified with EPDM or ABS; and polyamides condensed during processing ("RIM polyamide system").

(17) Polyureas, polyimides, polyamide-imides and polybenzoimidazoles.

(18) Polyesters deriving from dicarboxylic acids and diols and/or from hydroxycarboxylic acids or from the corresponding lactones such as, for example, polyethylene terephthalate, polybutylene terephthalate, poly-1,4-dimethylolcyclohexane terephthalate and polyhydroxybenzoates, as well as block copolyether esters deriving from polyethers with hydroxyl-terminated groups; and also polyesters modified with polycarbonates or MBS.

(19) Polycarbonates and polyester carbonates.

(20) Polysulfones, polyethersulfones and polyetherketones.

(21) Cross-linked polymers deriving from aldehydes on the one hand and from phenols, urea and melamines on the other, such as, for example, phenol/formaldehyde resins, urea/formaldehyde resins and melamine/formaldehyde resins.

(22) Drying or non-drying alkyd resins.

(23) Resins based on unsaturated polyesters deriving from copolyesters of dicarboxyl acids saturated and unsaturated with polyhydric alcohols and vinyl compounds as cross-linking agents, and also the above resins containing halogens and having a good flame-resistance.

(24) Cross-linkable acrylic resins deriving from substituted acrylates such as, for example, epoxy acrylates, urethane acrylates or polyester acrylates.

(25) Alkyd resins, resins based on polyesters or acrylated resins cross-linked with melamine resins, urea resins, resins based on polyisocyanates or epoxy resins.

(26) Cross-linked epoxy resins deriving from polyepoxides such as, for example, bis-glycidyl ethers or cycloaliphatic diepoxides.

(27) Natural polymers such as, for example, cellulose, rubber, gelatine, and their derivatives chemically modified to give homologous polymers such as, for example, cellulose acetates, propionates and butyrates, or cellulose ethers such as, for example, methyl-cellulose; as well as hydrocarbon resins ("rosins") or their derivatives.

(28) Mixtures of the above polymers ("polyblends") such as, for example, PP/EPDM, polyamides/EPDM or ABS, PVC/EVA, PVC/ABS, PVC/MBS, PC/ABS, PBTP/ABS, PC/ASA, PC/PBT, PVC/CPE, PVC/acrylates, POM/thermoplastics PUR, PC/thermoplastics PUR, POM/acrylates, POM/MBS, PPO/HIPS, PPO/PA 6.6 and copolymers, PA/HDPE, PA/PP, PA/PPO.

In particular, organic polymers which can be light-stabilized by the addition of the compounds having general formula (I) described above, are polyolefins, preferably polypropylene and polyethylene.

The addition of the compounds having general formula (I) of the present invention to the above organic polymers, is carried out according to methods known in the art.

For example, the compounds having general formula (I) can be added to the organic polymers, optionally in the presence of other additives, in the step following their preparation, or immediately before the transformation process.

For the above purposes, the compounds having general formula (I) are added to the polymer to be stabilized in a quantity ranging from 0.05% to 5% by weight, preferably between 0.01% and 2%.

The polymers stabilized as described above have a high resistance to degradation caused by light, in particular, ultraviolet radiation. They are therefore capable of maintaining their colour and brightness for a long period even when exposed to external agents.

The compositions having general formula (I) described above can also be used in the light-stabilization of compositions for coating or painting ("coating compositions") such as, for example, paints, lacquers, plastic-based compositions.

For the purposes of the present invention, coating or painting compositions are preferred in which the organic polymer is selected from:

(a) a thermoplastic polymer selected from thermoplastic polymers containing heteroatoms, in particular nitrogen, sulfur and/or oxygen, in the main chain, styrene copolymers, grafted styrene polymers and polymethyl methacrylates (PMMA); or (b) a paint ligand.

Specific examples of thermoplastic polymers (a) containing heteroatoms, in particular nitrogen, sulfur and/or oxygen, in the main chain, are listed above under points 13 to 20. Among these, polycarbonates, polyesters, polyamides, polyacetals, polyphenylene oxides and polyphenylene sulfides are preferred; particularly preferred are polycarbonates, polyesters such as, for example, polyethylene terephthalate (PET), and polyamides (PA) such as, for example, PA 6 and PA 6/6; polycarbonates are even more preferred.

Specific examples of styrene copolymers and grafted styrene polymers (a) are listed above under points 6 and 7.

Paint ligands (b) can comprise at least one of the organic polymers specified above. Specific examples of paints containing specific ligands are:

1. paints based on alkyd resins, acrylic resins, polyester resins, epoxy resins or melamine resins, which can be cross-linked at a low or high temperature, or mixtures of these resins, to which a cross-linking agent is optionally added;
2. polyurethane paints with two components based on acrylic resins containing hydroxyl groups, polyester resins or polyether resins and aliphatic or aromatic isocyanates, isocyanurates or polyisocyanates;
3. polyurethane paints with one component based on block isocyanates, isocyanurates or polyisocyanates which are unblocked during oven treatment;
4. paints with two components based on (poly)ketoimines and aliphatic or aromatic isocyanates, isocyanurates or polyisocyanates;
5. paints with two components based on (poly)ketoimines and an unsaturated acrylic resin or a polyacetoacetate resin or a methyl metha crylamidoglycolate;
6. paints with two components based on polyacrylates containing a carboxylic group or an amine group and polyepoxides;
7. paints with two components based on acrylic resins containing an anhydride group and a polyhydroxyl or polyamine compound;
8. paints with two components based on (poly)-oxazoline and acrylic resins containing an anhydride group or unsaturated acrylic resins or aliphatic or aromatic isocyanates, or isocyanurates or polyisocyanates;
9. paints with two components based on unsaturated polyacrylates and polymalonates;
10. thermoplastic polyacrylic paints based on thermoplastic acrylic resins or non-self-crosslinking acrylic resins combined with etherified melamine resins;
11. systems for paints based on siloxane-modified acrylic resins;
12. systems for paints based on fluoro-modified acrylic resins; and
13. systems for paints based on allyl glycidyl ethers.

The paints can be applied as one or two layers ("one- or two-coat") of coating and the stabilizing compounds having formula (I) are preferably added to the upper colourless coating.

The paints can be applied to the substrate (metal, plastic, wood, etc.) using the conventional methods such as, for example, brushing, spraying, pouring, dipping or electrophoresis.

A preferred embodiment of the present invention consists in paints or coatings (for example car coatings) comprising at least one compound having general formula (I). Ligands which can be used for the purpose are, for example, those listed above.

The compounds having general formula (I) of the present invention can be combined, as already mentioned above, with other conventional additives or their mixtures. These additives are added in a quantity ranging from about 0.1% to about 5% by weight of the weight of the polymeric compositions to be stabilized, preferably from about 0.5% to about 3% by weight. Some of the additives used are listed below as an example.

1. Antioxidants 1.1 Alkylated monophenols such as, for example:
   2,6-di-t-butyl-4-methylphenol;
   2-t-butyl-4,6-dimethylphenol;
   2,6-di-t-butyl-4-ethylphenol;
   2,6-di-t-butyl-4-n-butylphenol;
   2,6-di-t-butyl-4-isobutylphenol;
   2,6-di-cyclopentyl-4-methylphenol;
   2-(α-methylcyclohexyl)-4,6-dimethylphenol;
   2,6-dioctadecyl-4-methylphenol;
   2,4,6-tricyclohexylphenol;
   2,6-di-t-butyl-4-methoxymethylphenol;
   2,6-di-nonyl-4-methylphenol;
   2,4-dimethyl -6-(1'-methylundec-1'-yl)phenol;
   2,4-dimethyl-6-(1'-methylhectadec-1'-yl)phenol;
   2,4-dimethyl-6-(1'-methyltridec-1'-yl)phenol; and their mixtures.

1.2 Alkylthiomethylphenols such as, for example:
   2,4-dioctylthiomethyl-6-t-butylphenol;
   2,4-dioctylthiomethyl-6-methylphenol;
   2,4-dioctylthiomethyl-6-ethylphenol;
   2,6-didodecylthiomethyl-4-nonylphenol.

1.3 Hydroquinones and alkylated hydroquinones such as, for example:
   2,6-di-t-butyl-4-methoxyphenol;
   2,5-di-t-butylhydroquinone;
   2,5-di-t-amylhydroquinone;
   2,6-diphenyl-4-octadecyloxyphenol;
   2,6-di-t-butylhydroquinone;
   2,5-di-t-butyl-4-hydroxyanisol;
   3,5-di-t-butyl-4-hydroxyanisol;
   3,5-di-t-butyl-4-hydroxyphenyl stearate;
   bis(3,5-di-t-butyl-4-hydroxyphenyl)adipate.

1.4 Tocopherols such as, for example:
   α-tocopherol, β-tocopherol, γ-tocopherol, δ-tocopherol and their mixtures (Vitamin E).

1.5 Hydroxylated thiodiphenyl ethers such as, for example:
  2,2'-thiobis-(6-t-butyl-4-methylphenol);
  2,2'-thiobis-(4-octylphenol);
  4,4'-thiobis-(6-t-butyl-3-methylphenol);
  4,4'-thiobis-(6-t-butyl-2-methylphenol);
  4,4'-thiobis-(3,6-di-sec-amylphenol);
  4,4'-bis-(2,6-dimethyl-4-hydroxyphenyl)disulfide.
1.6 Alkylidene-bisphenols such as, for example:
  2,2'-methylenebis-(6-t-butyl-4-methylphenol);
  2,2'-methylenebis-(6-t-butyl-4-ethylphenol);
  2,2'-methylenebis[4-methyl-6-(α-methylcyclohexyl)phenol];
  2,2'-methylenebis(4-methyl-6-cyclohexylphenol);
  2,2'-methylenebis(6-nonyl-4-methylphenol);
  2,2 '-methylenebis(4, 6-di-t-butylphenol);
  2,2'-ethylidenebis(4,6-di-t-butylphenol);
  2,2'-ethylidenebis(6-t-butyl-4-isobutylphenol);
  2,2'-methylenebis [6-(α-methylbenzyl)-4-nonylphenol];
  2,2'-methylenebis[6-(α,α-dimethylbenzyl)-4-nonylphenol];
  4,4'-methylenebis(2,6-di-t-butylphenol);
  4,4'-methylenebis(6-t-butyl-2-methylphenol);
  1,1-bis-(5-t-butyl-4-hydroxy-2-methylphenyl)-butane;
  2,6-bis-(3-t-butyl-5-methyl-2-hydroxybenzyl)-4-methylphenol;
  1,1,3-tris-(5-t-butyl-4-hydroxy-2-methylphenyl)-butane;
  1,1-bis-(5-t-butyl-4-hydroxy-2-methyl-phenyl)-3-n-dodecylmercaptobutane;
  ethyleneglycol bis[3,3-bis(3'-t-butyl-4'-hydroxy-phenyl)butyrate];
  bis(3-t-butyl-4-hydroxy-5-methylphenyl)dicyclopentadiene;
  bis[2-(3'-t-butyl-2'-hydroxy-5'-methylbenzyl)-6-t-butyl-4-methylphenyl]terephthalate;
  1,1-bis(3,5-dimethyl-2-hydroxyphenyl)butane;
  2,2-bis(3,5-di-t-butyl-4-hydroxyphenyl)propane;
  2,2-bis(5-t-butyl-4-hydroxy-2-methylphenyl)-4-n-dodecylmercaptobutane;
  1,1,5,5-tetra (5-t-butyl-4-hydroxy-2-methylphenyl)pentane.
1.7 Benzyl compounds containing O, N or S such as, for example:
  3,5,3',5'-tetra-t-butyl-4,4'-dihydroxydibenzyl ether;
  octadecyl-4-hydroxy-3,5-dimethylbenzylmercaptoacetate;
  tris (3,5-di-t-butyl-4-hydroxybenzyl)amine;
  bis (4-t-butyl-3-hydroxy-2, 6-dimethylbenzyl) dithioterephthalate;
  bis (3, 5-di-t-butyl-4-hydroxybenzyl)sulfide;
  iso-octyl-3,5-di-t-butyl-4-hydroxybenzylmercaptoacetate;
1.8 Hydroxybenzylated malonates such as, for example:
  dioctadecyl-2,2-bis(3,5-di-t-butyl-2-hydroxybenzyl)malonate;
  dioctadecyl-2-(3-t-butyl-4-hydroxy-5-methylbenzyl)malonate;
  didodecylmercaptoethyl-2,2-bis(3,5-di-t-butyl-4-hydroxybenzyl)malonate;
  bis[4-(1,1,3,3-tetramethylbutyl)phenyl]-2,2-bis(3,5-di-t-butyl-4-hydroxybenzyl)malonate.

1.9 Aromatic hydroxybenzyl compounds such as, for example:
  1,3,5-tris(3,5-di-t-butyl-4-hydroxybenzyl)-2,4,6-trimethylbenzene;
  1,4-bis-(3,5-di-t-butyl-4-hydroxybenzyl)-2,3,5,6-tetramethylbenzene;
  2,4,6-tris(3,5-di-t-butyl-4-hydroxybenzyl)phenol.
1.10 Triazine compounds such as, for example:
  2,4-bis(octylmercapto)-6-(3,5-di-t-butyl-4-hydroxyaniline)-1,3,5-triazine;
  2-octylmercapto-4,6-bis(3,5-di-t-butyl-4-hydroxyaniline)-1,3,5-triazine;
  2-octylmercapto-4,6-bis(3,5-di-t-butyl-4-hydroxyphenoxy)-1,3,5-triazine;
  2,4,6-tris-(3,5-di-t-butyl-4-hydroxyphenoxy)-1,2,3-triazine;
  1,3,5-tris(3, 5-di-t-butyl-4-hydroxybenzyl)isocyanurate;
  1,3, 5-tris (4-t-butyl-3-hydroxy-2, 6-dimethylbenzyl) isocyanurate;
  2,4,6-tris- (3, 5-di-t-butyl-4-hydroxyphenylethyl)-1,3,5-triazine;
  1,3,5-tris(3,5-di-t-butyl-4-hydroxyphenylpropionyl)hexahydro-1,3,5-triazine;
  1,3,5-tris-(3,5-dicyclohexyl-4-hydroxybenzyl)isocyanurate.
1.11 Benzylphosphonates such as, for example:
  dimethyl-2,5-di-t-butyl-4-hydroxybenzylphosphonate;
  diethyl-3,5-di-t-butyl-4-hydroxybenzylphosphonate;
  dioctadecyl-3,5-di-t-butyl-4-hydroxybenzylphosphonate;
  dioctadecyl-5-t-butyl-4-hydroxy-3-methylbenzylphosphonate;
  calcium salts of monoethyl ester of 3,5-di-t-butyl-4-hydroxybenzylphosphonic acid.
1.12 Acylaminophenols such as, for example:
  4-hydroxylauranilide;
  4-hydroxystearanilide;
  octyl-N-(3,5-di-t-butyl-4-hydroxyphenyl)carbamate.
1.13 Esters of 6-(3,5-di-t-butyl-4-hydroxyphenyl) propionic acid with monohydric or polyhydric alcohols such as, for example:
  methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thioundecanol, 3-thiopentadecanol, trimethylhexandiol, trimethylolpropane, 4-hydroxymethyl-1-phospho-2,6,7-trioxabicyclo[2.2.2]octane.
1.14 Esters of β-(5-t-butyl-4-hydroxy-3-methylphenyl) propionic acid with monohydric or polyhydric alcohols such as, for example:
  methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thioundecanol, 10 3-thiopentadecanol, trimethylhexandiol, trimethylolpropane, 4-hydroxymethyl-1-phospho-2,6,7-trioxabicyclo[2.2.2]octane.
1.15 Esters of β-(3,5-dicyclohexyl-4-hydroxyphenyl) propionic acid with monohydric or polyhydric alcohols such as, for example: methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaery-thritol, tris(hydroxyethyl) isocyanurate, N,N'-bis (hydroxyethyl) oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.16 Esters of (3,5-di-t-butyl-4-hydroxyphenyl) acetic acid with monohydric or polyhydric alcohols such as, for example:

methanol, ethanol, octanol, octadecanol, 1,6-hexandiol, 1,9-nonandiol, ethylene glycol, 1,2-propanediol, neopentyl glycol, thiodiethylene glycol, diethylene glycol, triethylene glycol, pentaery-thritol, tris(hydroxyethyl) isocyanurate, N,N'-bis(hydroxyethyl)oxamide, 3-thioundecanol, 3-thiopentadecanol, trimethylhexandiol, trimethylolpropane, 4-hydroxymethyl-1-phospho-2,6,7-trioxabicyclo[2.2.2]octane.

1.17 Amides of β-(3,5-di-t-butyl-4-hydroxyphenyl)-propionic acid such as, for example: N,N'-bis(3,5-di-t-butyl-4-hydroxyphenylpropionyl)hexamethylenediamine; N,N'-bis(3,5-di-t-butyl-4-hydroxyphenylpropionyl) trimethylenediamine; N,N'-bis(3,5-di-t-butyl-4-hydroxyphenylpropionyl)hydrazine.

2. Ultra-violet ray and light-stabilizers.

2.1 Derivatives of 2-(2'-hydroxyphenyl) benzotriazoles such as, for example:

2-(2'-hydroxy-5methylphenyl) benzotriazole;

2-(3',5'-di-t-butyl-2'-hydroxyphenyl) benzotriazole;

2-(5'-t-butyl-2'-hydroxyphenyl) benzotriazole;

2-[2'-hydroxy-5'-(1,1,3,3-tetramethylbutyl)phenyl] benzotriazole;

2-(3',5', -di-t-butyl-2 '-hydroxyphenyl)-5-chlorobenzotriazole;

2-(3'-t-butyl-2'-hydroxy-5'-methylphenyl)-5-chlorobenzotriazole;

2-(3'-sec-butyl-5'-t-butyl-2'-hydroxyphenyl) benzotriazole;

2-(2'-hydroxy-4'-octyloxyphenyl) benzotriazole;

2-(3',5 '-di-t-amyl-2'-hydroxyphenyl) benzotriazole;

2-[3',5'-bis(α,α-dimethylbenzyl)-2'-hydroxyphenyl] benzotriazole;

mixtures of 2-[3'-t-butyl-2'-hydroxy-5'-(2-octyloxycarbonylethyl)phenyl)-5-chlorobenzotriazole, 2-[3'-t-butyl-5'-(2-(2-ethylhexyloxy) carbonylethyl)-2'-hydroxyphenyl]-5-chlorobenzotriazole, 2-[3'-t-butyl-2'-hydroxy-5'-(2-methoxycarbonylethyl) phenyl]-5-chlorobenzotriazole, 2-[3'-t-butyl-2'-hydroxy-5'-(2-methoxycarbonylethyl)phenyl benzotriazole, 2-[3'-t-butyl-2'-hydroxy-5'-(2-octyloxycarbonylethyl)phenyl] benzotriazole, 2-[3'-t-butyl-5'-(2-(2-ethylhexyloxy) carbonylethyl)-2'-hydroxyphenyl)benzotriazole, 2-(3'-dodecyl-2'-hydroxy-5'-methylphenyl)benzotriazole and 2-[3'-t-butyl 2'-hydroxy-5'-(2-iso-octyloxycarbonylethyl) phenyl]benzotriazole, 2,2'-methylene-bis[4-(1,1,-3,3-tetramethylbutyl)-6-benzotriazol-2-yl-phenol]; esterification product of 2-[3'-t-butyl-5'-(2-methoxycarbonylethyl)-2'-hydroxyphenyl]-2H-benzotriazole with polyethylene glycol 300;

[R—CH$_2$CH$_2$—COO(CH$_2$)$_3$]$_2$ wherein R=3'-t-butyl-4-hydroxy-5'-2H-benzotriazol-2-yl-phenyl.

2.2 Derivatives of 2-hydroxybenzophenones such as, for example: 4-hydroxy-; 4-methoxy-; 4-octyloxy-; 4-decyloxy-; 4-dodecyloxy-; 4-benzyloxy-; 4,2',4'-trihydroxy-; 2'-hydroxy-4,4'-dimethoxy.

2.3 Esters of benzoic acids, optionally substituted, such as, for example: phenyl salicylate, 4-t-butylphenyl salicylate, octylphenyl salicylate, benzoyl-resorcinol, bis(4-t-butylbenzoyl)-resorcinol, dibenzoyl-resorcinol, 2,4-di-t-butylphenyl-3,5-di-t-butyl-4-hydroxybenzoate, hexadecyl-3,5-di-t-butyl-4-hydroxybenzoate, octadecyl-3,5-di-t-butyl-4-hydroxybenzoate, 2-methyl-4,6-di-t-butyl-phenyl-3,5-di-t-butyl-4-hydroxybenzoate.

2.4 Acrylates such as, for example, ethyl or isoctyl α-cyano-β,β-diphenylacrylate; methyl α-carbomethoxycinnamate, methyl or butyl α-cyano-β-methyl-p-methoxycinnamate, methyl α-carbomethoxy-p-methoxy-cinnamate, N-(β-carbomethoxy-β-cyanovinyl)-2-methylindoline.

2.5 Nickel compounds such as, for example, complexes of 2,2'-thio-bis-[4-(1,1,3,3-tetramethylbutyl) phenol], for example 1:1 or 1:2 complexes, with or without additional ligands such as n-butylamine, triethanolamine or N-cyclohexyldiethanolamine, nickel dibutyldithiocarbamate, nickel salts of monoalkyl esters of 4-hydroxy-3,5-di-t-butyl-benzyl-phosphonic acid, such as methyl or ethyl esters, nickel complexes with ketoximes such as 2-hydroxy-4-methylphenyl undecyl ketoxime, nickel complexes of 1-phenyl-4-lauroyl-5-hydroxypyrazol with or without additional ligands.

2.6 Oxamides such as, for example:

4,4'-dioctyloxyoxanilide;

2,2'-diethoxyoxanilide;

2,2'-dioctyloxy-5,5'-di-t-butoxanilide;

2,2'-didodecyloxy-5,5'-di-t-butoxanilide;

2-ethoxy-2'-ethyloxanilide;

N,N'-bis (3-dimethylaminopropyl) oxamide;

2-ethoxy-5-t-butyl-2'-ethoxanilide and its mixtures with 2-ethoxy-2'-ethyl-5,4'-di-t-butoxanilide; and mixtures of disubstituted ortho- and paramethoxy anilides and mixtures of disubstituted ortho and para-ethoxy anilides.

2.7 2-(2-hydroxyphenyl)-1,3,5-triazines such as, for example:

2,4,6-tris (2-hydroxy-4-octyloxyphenyl)-1,3, 5-triazine;

2-(2-hydroxy-4-octyloxyphenyl)-4,6-bis(2,4-dimethylphenyl)-1,3,5-triazine;

2-(2,4-dihydroxyphenyl)-4,6-bis(2,4-dimethylphenyl)-1,3,5-triazine;

2,4-bis-(2-hydroxy-4-propyloxyphenyl)-6-(2,4-dimethylphenyl)-1,3,5-triazine;

2-(2-hydroxy)-4,6-bis(4-methylphenyl)-1, 3,5-triazine;

2-(2-hydroxy-4-dodecyloxyphenyl)-4,6-bis(2,4-dimethylphenyl)-1,3,5-triazine;

2-[2-hydroxy-4-(2-hydroxy-3-butyloxypropoxy) phenyl]-4,6-bis(2,4-dimethyl)-1,3,5-triazine;

2-[2-hydroxy-4-(2-hydroxy-3-octyloxy-propyloxy)-phenyl]-4,6-bis(2,4-dimethyl)-1,3,5-triazine.

3. "Metal-deactivators" such as, for example: N,N-diphenyloxamide, N-salicylal-N'-salicyloyl-hydrazine, N,N'-bis(salicyloyl)hydrazine; N,N'-bis(3,5-di-t-butyl-4-hydroxyphenylpropionyl) hydrazine, 3-salicyloylamino-1,2,4-triazole, bis(benzylidene)o-xalyl dihydrazide, oxanilide, isophthaloyl dihydrazide, sebacoyl bisphenylhydrazide, N,N'-diacetyladipoyl dihydrazide, N,N'-bis(salicyloyl) oxallyl dihydrazide, N,N'-bis(salicyloyl)thiopropionyl dihydrazide.

5 4. Phosphites and phosphonites such as, for example: triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-t-butylphenyl)phosphite, diisodecyl pentaerythritol diphosphite, bis(2,4-di-t-butyl-phenyl) pentaerythritol diphosphite, bis(2,5-di-t-butyl-4-methylphenyl) pentaerythritol diphosphite, diisodecyloxy-pentaerythritol diphosphite, bis (2,4-di-t-butyl-6-methylphenyl) pentaerythritol diphosphite, bis[2,4,5-tris(t-butylphenyl)]pentaerythritol diphosphite, tristearyl sorbitol triphosphite, tetrakis-(2,4-di-t-butyl-phenyl)-4,4'-diphenylilenediphosphonite, 5-iso-octyloxy-2,4,8,10-tetra-t-butyl-12H-di-benzo[d,g]-1,3,2-dioxaphosphocine, 6-fluoro-2,4,8,10-tetra-t-butyl-12-methyl-dibenzo[d,g]-1,3,2-dioxaphosphocine, bis(2,4-di-t-butyl-6-methylphenyl) methylphosphite, bis(2,4-di-t-butyl-6-methylphenyl) ethylphosphite.

5. Agents which are capable of destroying peroxides such as, for example, esters of β-thiodipropionic acid such as lauryl, stearyl, myristyl or tridecyl esters, mercaptobenzimidazole or zinc salt of 2-mercaptobenzimidazole, zinc dibutyldithiocarbamate, dioctadecyldisulfide pentaerythritol tetrakis (β-dodecylmercapto) propionate.

6. Stabilizers of polyamides such as, for example, copper salts combined with compounds of iodine and/or phosphorous, divalent manganese salts.

7. Basic co-stabilizers such as, for example: melamine, polyvinylpyrrolidone, dicyanodiamide, triallyl cyanurate, derivatives of urea, derivatives of hydrazine, amines, polyamides, polyurethanes, salts of alkaline metals and salts of earth-alkaline metals of fatty acids such as, for example, Ca-stearate, Zn-stearate, Mg-stearate, Mg-behenate, Na-ricinoleate, K-palmitate, antimo-nium-pyrocatecholate, t-in-pyrocatecholate.

8. Nucleating agents such as, for example: 4-t-butyl-benzoic acid, adipic acid, diphenylacetic acid.

9. Fillers and reinforcing agents such as, for example: calcium carbonate, silicates, glass fibres, asbestos, talc, kaolin, mica, barium sulfate, metal oxides and hydroxides, carbon black, graphite.

10. Other additives such as, for example: plasticizers, lubricants, emulsifying agents, pigments, optical brighteners, flame-retardants (for example, bromides, chlorurates, phosphorates and phosphorous/halogen mixtures), antistatic agents, blowing agents, thiosynergizing agents such as, for example, dilauryl thiodipropionate or distearyl thiodipropionate.

11. Benzofuranones and indolinones such as, for ex.:
   3-[4-(2-acetoxyethoxy)phenyl]-5,7-di-t-butylbenzofuran-2-one;
   5,7-di-t-butyl-3-[4-(2-stearoyloxyethoxy)phenyl] benzofuran-2-one;
   3,3', -bis [5,7-di-t-butyl-3-[4-(2-hydroxyethoxy)phenyl] benzofuran-2-one];
   5,7-di-t-butyl-3-(4-ethoxyphenyl) benzofuran-2-one;
   3-(4-acetoxy-3,5-dimethylphenyl)-5,7-di-t-butyl-benzofuran-2-one;
   3-(3,5-dimethyl-4-pivaloyloxyphenyl)-5,7-di-t-butyl-benzofuran-2-one; or those described in U.S. Pat. Nos. 4.325.863, 4.338.244, 5.175.312, 5.216.052, 5.252.643, 4.316.611, 4.316.622, 4.316.876 or in European patent applications 589.839 and 591.102.

Some illustrative but non-limiting examples are provided for a better understanding of the present invention and for its embodiment.

EXAMPLE 1

Preparation of β-methoxyethylamine crotonate of 4-(2,2,6,6-tetramethyl)piperidinyl (Compound Nr. 1) having the following formula:

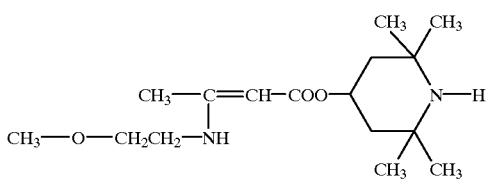

24.13 g (0.1 moles) of 2,2,6,6-tetramethyl-4-piperidinyl-acetoacetate, 24 g of toluene, 7.51 g (0.1 moles) of 2-methoxyethylamine and 0.23 g of glacial acetic acid, are charged into a 250 ml four-necked reactor, equipped with a stirrer, thermometer and reflux condenser with a water separator.

The reaction mass is maintained under stirring and reflux heated for 4 hours, to a temperature ranging from 115° C. to 118° C. During this period there is the formation of reaction water which is separated by azeotropic distillation: 1.5 g of reaction water are separated.

The solvent and acetic acid are removed by distillation and the raw residue thus obtained is subjected to fractionated distillation.

This distillation is carried out in a distiller consisting of a 100 ml boiler equipped with a thermometer, stirrer, column, condenser and device for the collection of fractions.

A central fraction containing 26.6 g of distilled product corresponding to Compound Nr. 1, is collected from the above distillation, operating under the following conditions:
   temperature at the head: 146° C.–151° C.;
   temperature of the boiler: 148° C.–152° C.;
   vacuum: 0.1 mm/Hg.

Compound Nr. 1 thus obtained, analyzed by gas-chromatography (GC), proves to be 97.5% pure, with a yield of about 89.2%.

Compound Nr. 1 is characterized by NMR analysis which confirms its enamine structure.

$^1$H-NMR (200 MHz, CDCl$_3$-TMS) δ (ppm): NH (broad) 8.50 ppm; C=CH (s) 4.34 ppm; the other signals are in accordance with the structure.

The other compounds (Compounds Nr. 2–9) are prepared analogously to Example 1, of which only the reaction conditions and characteristics are specified.

EXAMPLE 2

Preparation of β-(2,2,6,6,-tetramethylpiperidine-4-amino) ethyl crotonate (Compound Nr. 2) having the following formula:

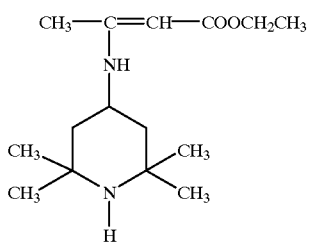

Amine: 4-amino-2,2,6,6-tetramethylpiperidine; 31.25 g (0.2 moles).

Carbonyl compound: ethyl acetoacetate; 26.03 g (0.2 moles)

Solvent: toluene; 50 g.

Catalyst: acetic acid; 0.3 g

Reaction water separated: 3.3 g

Duration and reaction temperature: 5 hours at 126° C.–128° C.

Distillation range: 118° C.–133° C. (head); 130° C.–144° C. (boiler); 0.10 mm/Hg–0.15 mm/Hg (vacuum).

Product obtained: 47.5 g.

GC Purity: 98.9%.

Yield: 88.4%

$^1$H-NMR (200 MHz, CDCl$_3$-TMS) δ (ppm): NH (d) 8.39 ppm; C=CH (s) 4.35 ppm; the other signals are in accordance wish the structure.

EXAMPLE 3

Preparation of β-(2,2,6,6,-tetramethylpiperidine-4-amino) crotonate of 4-(2,2,6,6-tetramethyl) piperidinyl (Compound Nr. 3) having the following formula:

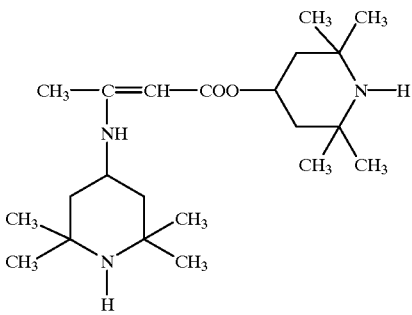

Amine: 4-amino-2,2,6,6-tetramethylpiperidine; 31.25 g (0.2 moles).

Carbonyl compound: 2,2,6,6-tetramethyl-4-piperidinylacetoacetate; 48.5 g (0.2 moles).

Solvent: toluene; 50 g.

Catalyst: acetic acid; 0.3 g

Reaction water separated: 3.44 g

Reaction time and temperature: 3.5 hours at 114° C.–128° C.

In this case the raw residue obtained is not subjected to fractionated distillation as the endproduct crystallizes in the reaction medium at room temperature. When the crystallization is complete, the product obtained is filtered, washed with toluene and dried.

Product obtained: 41.4 g.

GC Purity: 98.9%.

Yield: 54.4%

$^1$H-NMR (200 MHz, CDCl$_3$-TMS) δ (ppm): NH (d) 8.32 ppm; C=CH (s) 4.30 ppm, the other signals are in accordance with the structure.

Melting point: 151° C.

EXAMPLE 4

Preparation of 4-piperidino-2,2,6,6-tetramethyl-1,2,-5,6-tetrahydropyridine (compound Nr. 4) having the following formula:

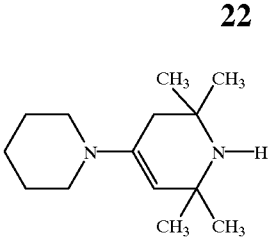

Compound Nr. 4 is synthesized operating according to the procedure described by M. Dagonneau et al. in "Synthesis" (1984), page 902. The product obtained has a purity >99%.

EXAMPLE 5

Preparation of β-(2,2,6,6-tetramethylpiperidine-4-amino)t-butyl crotonate (compound Nr. 5) having the following formula:

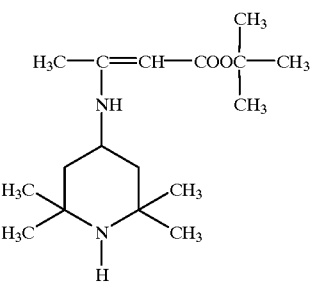

Amine: 4-amino-2,2,6,6-tetramethylpiperidine; 31.25 g (0.2 moles).

Carbonyl compound: t-butyl acetoacetate; 31.64 g (0.2 moles).

Solvent: toluene; 50 g.

Catalyst: acetic acid; 0.3 g

Reaction water separated: 3.2 g

Reaction time and temperature: 5 hours at 122° C.–123° C.

Distillation range: 142° C.–162° C. (head); 146° C.–183° C. (boiler); 0.10 mm/Hg (vacuum).

Product obtained: 37.1 g.

GC Purity: 91.6%.

Yield: 62.6%

Melting point: 86.7° C. (solid at room temperature).

EXAMPLE 6

Preparation of β-(2,2,6,6-tetramethylpiperidine-4-amino) octadecyl crotonate (Compound Nr. 6) having the following formula:

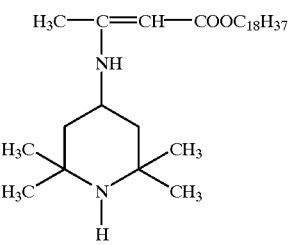

Amine: 4-amino-2,2,6,6-tetramethylpiperidine; 13.22 g (0.085 moles).

Carbonyl compound: octadecyl acetoacetate; 30 g (0.085 moles).

Solvent: toluene; 25 g.

Catalyst: acetic acid; 0.15 g

Reaction water separated: 1.21 g

Reaction time and temperature: 3 h 45' at 132° C.–138° C.

In this case the raw reaction mass is not subjected to fractionated distillation as the end-product crystallizes in the reaction medium at room temperature. When the crystallization is complete, the product obtained is filtered, washed with toluene and dried.

Product obtained: 21.7 g.

GC Purity: 99%.

Yield: 51.8%

Melting point: 53.7° C.

EXAMPLE 7

Preparation of 1-phenyl-1-(2,2,6,6-tetramethylpiperidine-4-amino)-2-benzoyl-ethylene (Compound Nr. 7) having the following formula:

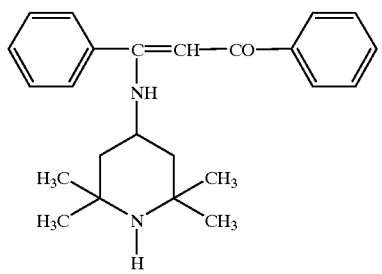

Amine: 4-amino-2,2,6,6-tetramethylpiperidine; 38.57 g (0.247 moles).

Carbonyl compound: dibenzoyl methane; 44.85 g (0.2 moles).

Solvent: toluene; 50 g.

Catalyst: acetic acid; 0.9 g

Reaction water separated: 4.8 g.

Reaction time and temperature: 22 h at 159° C.–163° C.

In this case the raw reaction mass is not subjected to fractionated distillation as the end-product crystallizes in the reaction medium at room temperature When the crystallization is complete, the product obtained is filtered, washed with toluene and dried.

Product obtained: 32.25 g.

GC Purity: 92%.

Yield: 44.5%

Melting point: 99° C.

EXAMPLE 8

Preparation of β-(2,2,6,6-tetramethyl-piperidine-4-amino) anilide crotonate (Compound Nr. 8) having the following formula:

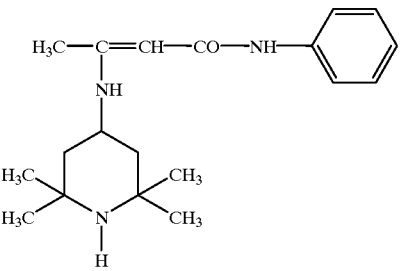

Amine: 4-amino-2,2,6,6-tetramethylpiperidine; 31.25 g (0.2 moles).

Carbonyl compound: aceto-acetanilide; 35.44 g (0.2 moles).

Solvent: methanol; 100 g.

Catalyst: acetic acid; 0.4 g

Reaction water separated: in this case the reaction water is not separated.

Reaction time and temperature: 13 h at 20° C.–26° C.

In this case the raw reaction mass is not subjected to fractionated distillation as the end-product crystallizes in the reaction medium at room temperature. When the crystallization is complete, the product obtained is filtered, washed with n-pentane and dried.

Product obtained: 54.34 g.

GC Purity: >97%.

Yield: 86.1%

Melting point: 188° C.

EXAMPLE 9

Preparation of 1-methyl-1-(2,2,6,6,-tetramethyl-piperidine-4-amino)-2-benzoyl-ethylene (Compound Nr. 9) having the following formula:

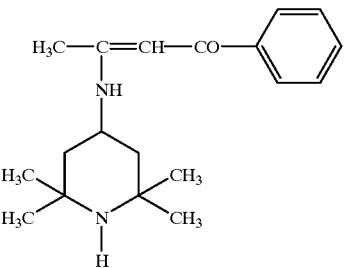

Amine: 4-amino-2,2,6,6-tetramethylpiperidine; 31.25 g (0.2 moles).

Carbonyl compound: benzoylacetone; 32.44 g (0.2 moles).

Solvent: toluene; 100 g.

Catalyst: acetic acid; 0.4 g

Reaction water separated: 3.2 g

Reaction time and temperature: 6 h at 118° C.–120° C.

In this case the raw reaction mass is not subjected to fractionated distillation as the end-product crystallizes in the reaction medium at room temperature. When the crystallization is complete, the product obtained is filtered, washed with n-pentane and dried.

Product obtained: 50.2 g.

GC Purity: >98.5%.

Yield: 83.5%

Melting point: 112° C.

EXAMPLE 10
Light Stabilization of Polypropylene.

Polypropylene of the type Moplen FLF 20 produced and sold by Montell is used for the purpose (MFI=9.2, at 230° C. and 21.6 kg).

100 g of the above polypropylene in powder form, are mixed with 0.25 g of the following compounds:

(A): Compound Nr. 1 obtained as described above;

(B): 2-hydroxy-4-n-octoxybenzophenone, known under the trade-name of Lowilite 22, produced and sold by Great Lakes;

(C): Compound Nr. 4 obtained as described above.

The homogeneous mixture thus obtained is subjected to extrusion in a Brabender extruder having a diameter of 19 mm and a length about 25 times the diameter, equipped with a screw and a 2 mm nozzle, with a compression ratio of 1:4 and with a temperature profile of 190° C., 210° C., 215° C., 215° C.

The extruder is activated at 50 rpm and the filament leaving the extruder is cut into granules which are subsequently transformed into films with a "Plasticizer" operating at a temperature of 220° C. The films are then subjected to compression until films with a thickness of 100 μm are obtained, operating under the following conditions: 2 minutes of preheating and 2 minutes of compression 100 Kg/cm$^2$ at 200° C.

The films thus obtained are subjected to accelerated aging in a first Atlas CI 65 Weatherometer under the following conditions (WOM 1):

temperature of the black panel: 63° C.;

radiation: 0.40 W/m$^2$ at 340 nm;

relative humidity: 50%;

rain cycle: (102'-18') 18' of rain every 102';

and, subsequently in a second Atlas CI 65 Weatherometer (WOM 2) under the following conditions:

temperature of the black panel: 60° C.;

radiation: 0.33 W/m$^2$ at 340 nm;

relative humidity: 50%.

For comparative purposes, a film obtained from polypropylene without light-stabilizers is prepared.

The breaking time (hrs) of the films is analyzed and the data are shown in Table 1.

TABLE 1

| Stabilizer | Breaking Time (hrs) | |
| --- | --- | --- |
|  | WOM 1 | WOM 2 |
| — | 105 | 180 |
| (A) | 419 | >700 |
| (B) | 115 | 456 |
| (C) | 115 | 203 |

The data shown in Table 1 clearly demonstrate that Compound Nr. 1 gives a much higher breaking strength than that provided by the light-stabilizer (B) known in the art whereas, although Compound Nr. 4 (C) is an enamine carrying a sterically hindered amine group in the molecule which does not belong, however, to the group of compounds having general formula (I), it does not provide breaking strength and, in fact, has a performance similar to that of non-stabilized polypropylene.

EXAMPLE 11
Light Stabilization of Polypropylene.

Polypropylene of the type Moplen FLF 20 produced and sold by Montell is used for the purpose (MFI=9.2 at 230° C. and 21.6 kg).

100 g of the above polypropylene in powder form, are mixed with 0.25 g of the following compounds:

(A): Compound Nr. 1 obtained as described above;

(B): Compound Nr. 2 obtained as described above;

(C): Compound Nr. 3 obtained as described above.

(D): bis(2,2,6,6-tetramethyl-4-piperidinyl) sebacate known under the trade-name of Tinuvin 770, produced and sold by Ciba Geigy.

The homogeneous mixture thus obtained is subjected to extrusion in a Brabender extruder having a diameter of 19 mm and a length about 25 times the diameter, equipped with a screw and a 2 mm nozzle, with a compression ratio of 1:4 and with a temperature profile of 190° C., 210° C., 215° C., 215° C.

The extruder is activated at 50 rpm and the filament leaving the extruder is cut into granules which are subsequently transformed into films with a "Plasticizer" operating at a temperature of 220° C. The films are then subjected to compression until films with a thickness of 60 μm are obtained, operating under the following conditions: 2 minutes of preheating and 2 minutes of compression 100 Kg/cm$^2$ at 200° C.

The films thus obtained are subjected to ultraviolet radiation in UV-CON under the following conditions:

8 h, with light, at 60° C.;

4 h, in the dark, with condensation, at 40° C.;

and to accelerated aging in an Atlas CI 65 Weatherometer under the following conditions (WOM 1):

temperature of the black panel: 63° C.;

radiation: 0.40 W/m$^2$ at 340 nm;

relative humidity: 50%;

rain cycle: (102'-18') 18' of rain every 102';

For comparative purposes, a film obtained from polypropylene without light-stabilizers is prepared.

The breaking time (hrs) of the films is analyzed and the data are shown in Table 2.

TABLE 2

| Stabilizer | Breaking Time (hrs) | |
| --- | --- | --- |
|  | UV - CON | WOM 1 |
| — | 90 | 181 |
| (A) | 182 | 342 |
| (B) | 248 | 525 |
| (C) | 248 | 548 |
| (D) | 182 | 342 |

The data in Table 2 show that the stabilizing capacity of Compound Nr. 1 (A) is comparable to that of Tinuvin 770 (D) whereas the stabilizing capacity of Compound Nr. 2 (B) and Nr. 3 (C) is much higher than that of Tinuvin 770 (D).

EXAMPLE 12
Light Stabilization of Polyethylene.

Polyethylene of the type Riblene FC20 produced and sold by Polimeri Europa is used for the purpose.

100 g of the above polyethylene in powder form, are mixed with 0.25 g of the following compounds:

(A): Compound Nr. 1 obtained as described above;

(B): Compound Nr. 2 obtained as described above;

(C): Compound Nr. 3 obtained as described above.

(D): bis(2,2,6,6-tetramethyl-4-piperidinyl)sebacate known under the trade-name of Tinuvin 770, produced and sold by Ciba Geigy.

The homogeneous mixture thus obtained is subjected to extrusion in a Brabender extruder having a diameter of 19 mm and a length about 25 times the diameter, equipped with a screw and a 2 mm nozzle, with a compression ratio of 1:4 and with a temperature profile of 190° C., 210° C., 215° C., 215° C.

The extruder is activated at 50 rpm and the filament leaving the extruder is cut into granules which are subsequently transformed into films with a "Plasticizer" operating at a temperature of 220° C. The films are then subjected to compression until films with a thickness of 100 µm are obtained, operating under the following conditions: 2 minutes of preheating and 2 minutes of compression 100 Kg/cm² at 200° C.

The films thus obtained are subjected to accelerated aging in an Atlas CI 65 Weatherometer under the following conditions (WOM 1):

temperature of he black panel: 63° C.;

radiation: 0.40 W/m² at 340 nm;

relative humidity: 50%;

rain cycle: (102'-18') 18' of rain every 102';

For comparative purposes, a film obtained from polyethylene without light-stabilizers is prepared.

The breaking time (hrs) of the films is analyzed and the data are shown in Table 3.

TABLE 3

| Stabilizer | Breaking Time (hrs) WOM 1 |
|---|---|
| — | 280 |
| (A) | 480 |
| (B) | 450 |
| (C) | 480 |
| (D) | 409 |

The data in Table 3 show that the stabilizing capacity of Compound Nr. 1 (A), Nr. 2 (B) and Nr. 3 (C) is higher than that of Tinuvin 770 (D).

What is claimed is:

1. Organic polymer(s) light stabilized by the addition to said organic polymer(s) of a light stabilization effective amount of β-(2,2,6,6-tetramethylpiperidine-4-amino)ethyl crotonate.

2. Organic polymer(s) light stabilized by the addition to said organic polymer(s) of a light stabilization effective amount of β-(2,2,6,6-tetramethylpiperidine-4-amino)t-butyl crotonate.

3. Organic polymer(s) light stabilized by the addition to said organic polymer(s) of an effective amount of β-(2,2,6,6-tetramethylpiperidine-4-amino) octadecyl crotonate.

4. Organic polymer(s) light stabilized by the addition to said organic polymer(s) of a light stabilization effective amount of 1-phenyl-1-(2,2,6,6-tetramethylpiperidine-4-amino)-2-benzoyl-ethylene.

5. Organic polymer(s) light stabilized by the addition to said organic polymer(s) of a effective amount of β-(2,2,6,6-tetramethylpiperidine-4-amino)anilide crotonate.

6. Organic polymer(s) light stabilized by the addition to said organic polymer(s) of a light stabilization effective amount of 1-methyl-1-(2,2,6,6-tetramethylpiperidine-4-amino)-2-benzoyl-ethylene.

7. Organic polymer(s) according to any one of claims 1–6, wherein said amount is from 0.05% to 5% by weight.

8. Organic polymer(s) according to any one of claims 1–6, wherein said amount is from 0.01% to 2% by weight.

9. Organic polymer(s) according to any one of claims 1–6, wherein said organic polymer(s) are selected from the group consisting of polymers and copolymers of mono-olefins or diolefins; hydrocarbon resins; polymers and copolymers of styrene, α-methyl styrene or p-methylstyrene; halogenated polymers; polymers and copolymers of α, β unsaturated acids and esters; polymers and copolymers of unsaturated alcohols, unsaturated amines or acyl or acetal derivatives thereof; polymers and copolymers of cyclic ethers; polyacetals or modified polyacetals; polyphenylene oxides; polyphenylene sulfides, polyurethanes; polyamides or copolyamides; polyureas; polyimides; polyamide-imides; polybenzoimidazoles; polyesters; polycarbonates; polyester carbonates; polysulfones; polyether-sulfones; polyether ketones; polymers from aldehydes and phenols, urea or melamines; alkyd resins; epoxy resins and natural polymers or modified natural polymers, and mixtures thereof.

* * * * *